United States Patent [19]

Wagner et al.

[11] 4,286,660
[45] Sep. 1, 1981

[54] PROCESS AND INSTALLATION FOR THE FLOODING OF PETROLEUM DEPOSITS AND OIL SHALE

[75] Inventors: Fritz Wagner, Braunschweig-Stöckheim; Peter Rapp; Hans Bock, both of Brunswick; Walter Lindörfer, Kassel; Walther Schulz, Vechta; Wilhelm Gebetsberger, Barnstorf, all of Fed. Rep. of Germany

[73] Assignees: Gesellschaft für Biotechnologische Forschung GmbH; Wintershall Aktiengesellschaft, both of Fed. Rep. of Germany

[21] Appl. No.: 23,295

[22] Filed: Mar. 23, 1979

[51] Int. Cl.³ .................. E21B 43/22; C12M 1/02
[52] U.S. Cl. .................... 166/246; 166/266; 166/275; 252/8.55 D; 435/316
[58] Field of Search ........... 166/246, 273, 274, 275, 166/305 R, 266; 252/8.55 D; 435/316

[56] References Cited

U.S. PATENT DOCUMENTS

| | | | |
|---|---|---|---|
| 2,396,900 | 3/1946 | Taggart, Jr. | 166/246 X |
| 2,413,278 | 12/1946 | Zobell | 166/246 UX |
| 3,020,206 | 2/1962 | Patton et al. | 166/246 UX |
| 3,114,707 | 12/1963 | Hodge | 252/8.55 D |
| 3,201,327 | 8/1965 | Beck | 435/316 X |
| 3,340,930 | 9/1967 | Hitzman | 166/274 X |
| 4,096,073 | 6/1978 | Hitzman | 166/273 X |

FOREIGN PATENT DOCUMENTS

| | | | |
|---|---|---|---|
| 2646505 | 4/1978 | Fed. Rep. of Germany | 166/275 |
| 2646506 | 4/1978 | Fed. Rep. of Germany | 166/275 |
| 2646507 | 4/1978 | Fed. Rep. of Germany | 166/275 |

Primary Examiner—Stephen J. Novosad
Assistant Examiner—George A. Suchfield
Attorney, Agent, or Firm—Scully, Scott, Murphy & Presser

[57] ABSTRACT

A process and installation for the flooding of petroleum deposits and oil shale and, more particularly, through the use of dispersions of non-ionogenic, boundary surface-active materials in water as the flooding medium. For the flooding of petroleum-hydrocarbon materials from petroleum deposits and oil shale there can be utilized dispersions of non-ionogenic, boundary surface-active glycolipids, and such preferred structures can be employed which are produced from hydrocarbon mixtures as the C-source. This is effected in two stages with predetermined technological measures. In the first stage, there are initially produced glycolipids through microorganisms with alkane mixtures under predetermined parameters in semi- or continual process cycles and, in the second stage, separated from the cellular material through temperature, pH, osmotic shock. The formed glycolipids can also be separated from the cellular material with unpolarized, organic solvent media.

17 Claims, 2 Drawing Figures

PROCESS AND INSTALLATION FOR THE FLOODING OF PETROLEUM DEPOSITS AND OIL SHALE

The present invention relates to a process and installation for the flooding of petroleum deposits and oil shale and, more particularly, through the use of dispersions of non-ionogenic, boundary surface-active materials in water as the flooding medium.

The presently not published process for the flooding of petroleum deposits as set forth in German Pat. No. 26 46 507 describes non-ionic, boundary surface-active materials which are to be impressed as flooding media into the deposits in the absence of preflushing liquids. These operative materials consist of glycolipids of predetermined structures which should be isolated from microorganisms. In the formula of these materials, the disaccharide component consists of trehalose, cellobiose, maltose, and isomaltose. The alkyl groups of the substituents $R_1$ through $R_4$ can be unbranched, branched, saturated, unsaturated, and hydroxylized. For the stabilization of the aqueous dispersion there can be added other non-ionic, boundary surface-active materials.

These dispersions are produced, for example, with the deposit water. There should be formulated concentrations of 0.01 through 5 g/l.

The presently not published process for the flooding of petroleum deposits as disclosed in German Pat. No. 26 46 506 describes, in a further development of German Pat. No. 26 46 507, that glycolipids of predetermined structures are known and in whose formulas the mono-saccharide component should consist of glucose, fructose, mannose, or galactose. The alkyl groups $R_1$ through $R_5$ may similarly be unbranched, branched, saturated, unsaturated, and hydroxylized.

The presently not published process for the flooding of petroleum deposits pursuant to German Pat. No. 26 46 505 describes, in a further development of the process of German Pat. No. 26 46 507, that glycolipids of predetermined structure are known and whose oligosaccharide component should consist of amylopectin, amylose, cellulose, dextrans, chitin, yeast glucane (Hefeglukan), pullulan, and glycogen. The alkyl groups of the substituents $R_1$ through $R_3$ can similarly be unbranched, branched, saturated, unsaturated, and hydroxylized. These processes afford the advantage that the operative media which are introduced into the deposit together with the aqueous dispersion will not emit into the deposit precipitating products which include earth alkali and iron-ions tending to cause blockages. Through the use of these operative media of predetermined structures as aqueous dispersions, no superelevated infeed pressure is required since the viscosity of the flooding medium is not elevated by these materials. The technology for the improvement of yield in the secondary recovery of petroleum through water flooding is known from German Pat. No. 24 10 267. Pursuant to this process, through biosyntheses with growing submersed cultures of aerobic microorganisms there are produced operative media whose structures are not known. The operative media for the improved oil removal from the deposits should be conducted into the deposit as culture solutions or added to the flooding water. For the production of these submersed cultures, whose culture solution contains the effective or operative media, there should be utilized as the C- and energy source a petroleum-water mixture originating from the production of the petroleum.

This process avoids blockages of the deposit due to the cellular material which is separated from the culture solution. A further advantage inherent to this process is that, over a period of days, fermenters are utilized for the production of the aqueous culture solution, which afford a control over this process and controlling of the culture.

However, in accordance with the state of the art, this process is subject to the disadvantage that the structure of the produced operative medium is not known. Thus, it is not possible to produce these materials in the same optimum composition and concentration.

Accordingly, the process pursuant to the invention has as its object that for the flooding of petroleum-hydrocarbon materials from petroleum deposits and oil shale there be utilized dispersions of non-ionogenic, boundary surface-active glycolipids, and such preferred structures be employed which are produced from hydrocarbon mixtures as the C-source.

It is a further object of the process pursuant to the invention that this be effected in two stages with predetermined technological measures. In the first stage, there are initially produced glycolipids through microorganisms with alkane mixtures under predetermined parameters in semi- or continual process cycles and, in the second stage, separated from the cellular material through temperature, pH, osmotic shock. The formed glycolipids can also be separated from the cellular material with unpolarized, organic solvent media.

Thus, the process pursuant to the invention solves the problem of producing glycolipids through a biological method with the utilization of alkane mixtures, and to employ these for the improvement of the yield of petroleum from deposits and oil shale.

The invention proceeds from German Pat. No. 26 46 507 which describes the state of the art for increasing the yield of petroleum through the flooding of petroleum deposits. Described therein are processes which propose the utilization of microemulsions with surface-active or co-surface-active media for secondary petroleum recovery.

The therein mentioned German Pat. No. 14 83 770 proposes the production and utilization of a microemulsion of partial fatty esters of sorbitan, salts of the alkylaryl sulfonates, ethanol and a gasoline fraction.

A similar composition is described in German Published Patent No. 12 49 190.

These microemulsions utilize numerous materials, as well as oil or fractions produced therefrom which are to be recovered.

This state of the art proceeds from the point that there should be utilized emulsions with high viscosities for the secondary recovery of petroleum. These emulsions contain petrosulfonate, which together with Ca and/or Mg, Fe-ions of the deposit form precipitates leading to blockages of the pores of the deposit. Consequently, it is necessary to utilize high infeed pressures for the impressing of such emulsions.

The aqueous dispersion according to the process of the invention is more simply constructed and does not necessitate such additive media. These utilize a non-ionogenic operative medium which will not produce precipitates in the deposit. This aqueous dispersion also does not influence the viscosity of the flooding medium and therefore does not require any excessive infeed pressure.

German Pat. No. 24 10 267 renders known an installation for the secondary recovery of petroleum. In accordance with this state of the art, a part of the quantity of the petroleum-water mixture originating from the production is conducted directly into a bioreactor into which there have been additionally introduced nutrients, growth-enhancing materials, acid, leaching materials, and contaminated air removed. The produced four-phase mixture is conducted to a filter, the cellular material removed therefrom, thereafter the culture solution is conveyed into a separator in which the residual oil is separated therefrom, and then the culture solution is added to the flooding water for the injecting bore. This installation has the disadvantage that the petroleum-water mixture is conducted directly into the reactor and that, initially, an oil-containing cellular quantity and thereafter the residual petroleum is separated and the culture solution is added directly to the flooding water. In contrast therewith, the installation pursuant to the invention first separates the water and petroleum in a separator and conducts the petroleum in a partial quantity into the bioreactor of the first stage, in which there preferably is also introduced n-alkane, as well as a nutrient salt solution and the deposit water, air or oxygen-enriched air is added and contaminated air is removed. The phase mixture is then introduced into a separator and therein the unused residual oil is then separated and the phase mixture then introduced into the bioreactor of the second stage. In this, as described in an exemplary manner, there is carried out the temperature, pH or osmotic shock for the recovery of a higher concentration of glycolipids. The oil-free culture suspension is then divided in the subsequent separator into the separated and occasionally recycled cellular material and into the aqueous phase containing the glycolipids. The latter is then converted in the mixer with a stirring device by means of dissolvent intermediaries and/or dispersing medium into a stable dispersion. This is then metered into the flooding water or introduced directly into the flooding bore.

In a modification of this installation, the cellular material is separated from the aqueous phase and the residual oil in a separator and, thereafter, the cellular material extracted in an extractor with introduced or recycled extraction medium, a raw extract recovered in a vaporizer and dispersed in a mixer in the same manner.

The process of the invention utilizes glycolipids as the operative medium, which are produced with hydrocarbon-enriched microorganisms, and through temperature, pH, osmotic shock or through extraction separated from the cellular material.

BRIEF DESCRIPTION OF THE DRAWINGS

The installation for effectuation of the process of the invention is also described in connection with FIGS. 1 and 2 of the drawings each illustrating an embodiment of said process. The effectuation of the process of the invention is described in Examples 1 through 4. Example 5 illustrates the production of a stable dispersion. Examples 6 and 7 illustrate the technical advance of the improved yield of petroleum.

DESCRIPTION OF THE PREFERRED EMBODIMENTS

Figure 1:
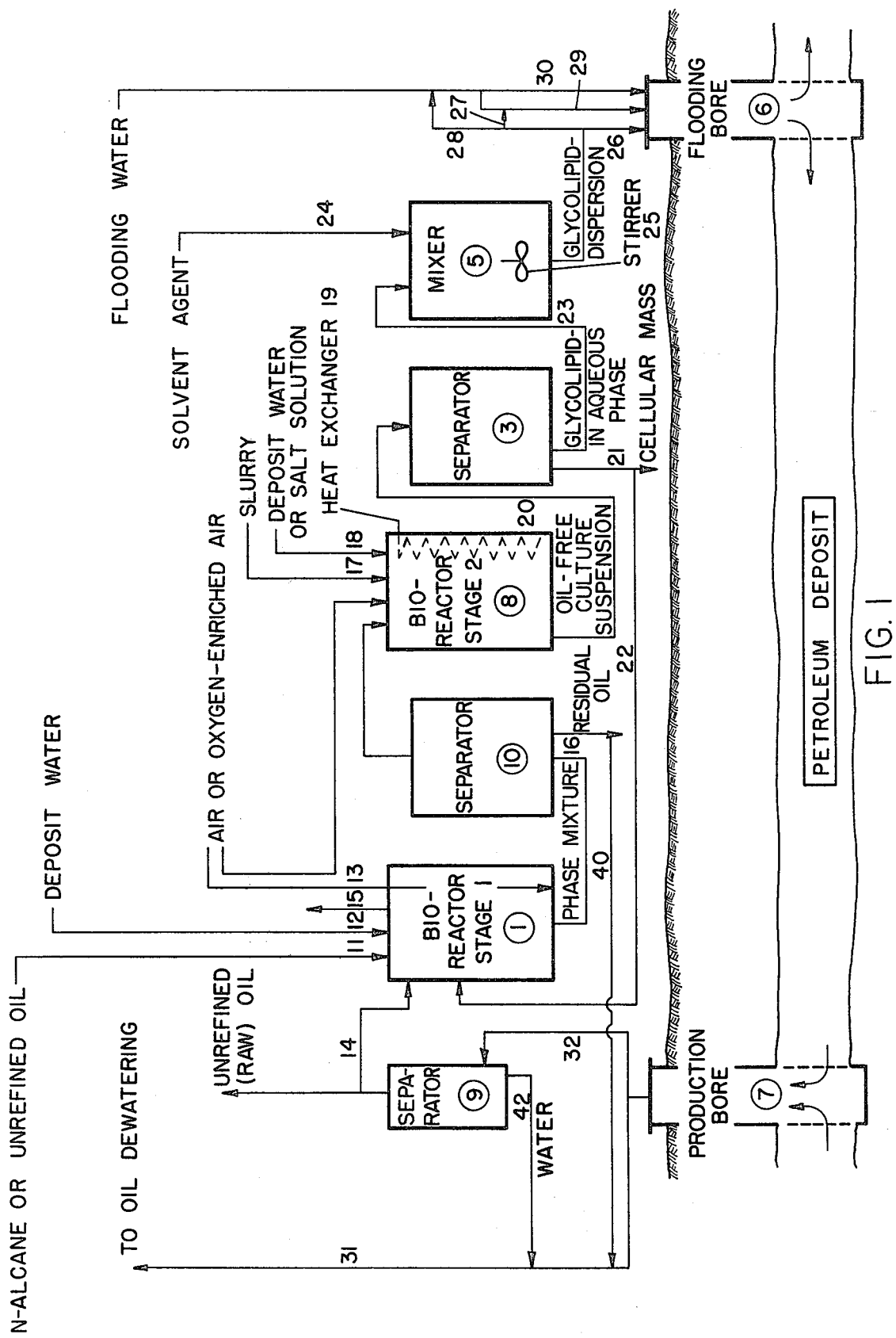

According to FIG. 1, bioreactor 1 (stage 1) equipped with a mechaical stirrer is filled with an n-alkane or crude petroleum through line 11 inoculated with *Norcardia rhodochrous* sp., crude petroleum through line 14 (following separation from flooding water in separator unit 9), deposit water through line 12 and air or oxygen-enriched air through line 13. Gaseous effluent from bioreactor 1 is released to the atmosphere through line 15. Following a period of cultivation, the suspension of alkane/unrefined petroleum and microorganisms is conducted from bioreactor 1 through line 16 into separator unit 10 wherein separation of the culture suspension from the residual oil is effected. The substantially oil-free culture suspension is thereafter introduced into bioreactor 8 (stage 2) equipped with heat exchange coil 19 and fed with air or oxygen enriched air, slurry through line 17 and deposit water or salt solution through line 18. The culture suspension undergoes temperature shock in bioreactor 1 thereby releasing an intracellular glycolipid-containing liquid which is introduced into separator unit 3 to separate the glycolipid from the remaining cellular mass, the latter being cycled through line 22 to bioreactor 1. The glycolipid recovered from separator unit 3 is passed through line 23 to mixer 5 equipped with stirrer 25 and combined with dispersant through line 24. Th resulting glycolipid dispersion flowing through line 26, together with flooding water flowing through line 30, is thereafter introduced into flooding bore 6 through any of lines 26, 27, 28 and/or 29 to effect extraction of petroleum. Residual oil recovered from the microorganisms in separator 10 is conducted through lines 40 and 31 to be used, as desired, for further oil dewatering. Recovered petroleum together with glycolipid-containing flooding water is recovered from production bore 7 and passes to separator unit 9 where it is separated into a crude petroleum fraction and a flooding water fraction. Part of the crude petroleum is introduced into bioreactor 1 as substrate for cultivating inoculum, the remaining portion (i.e., the major part) of the crude representing the recovered petroleum deposit. Water recovered in separator 9 is combined with recycle water in line 40 and can be used to effect further oil dewatering.

Figure 2:
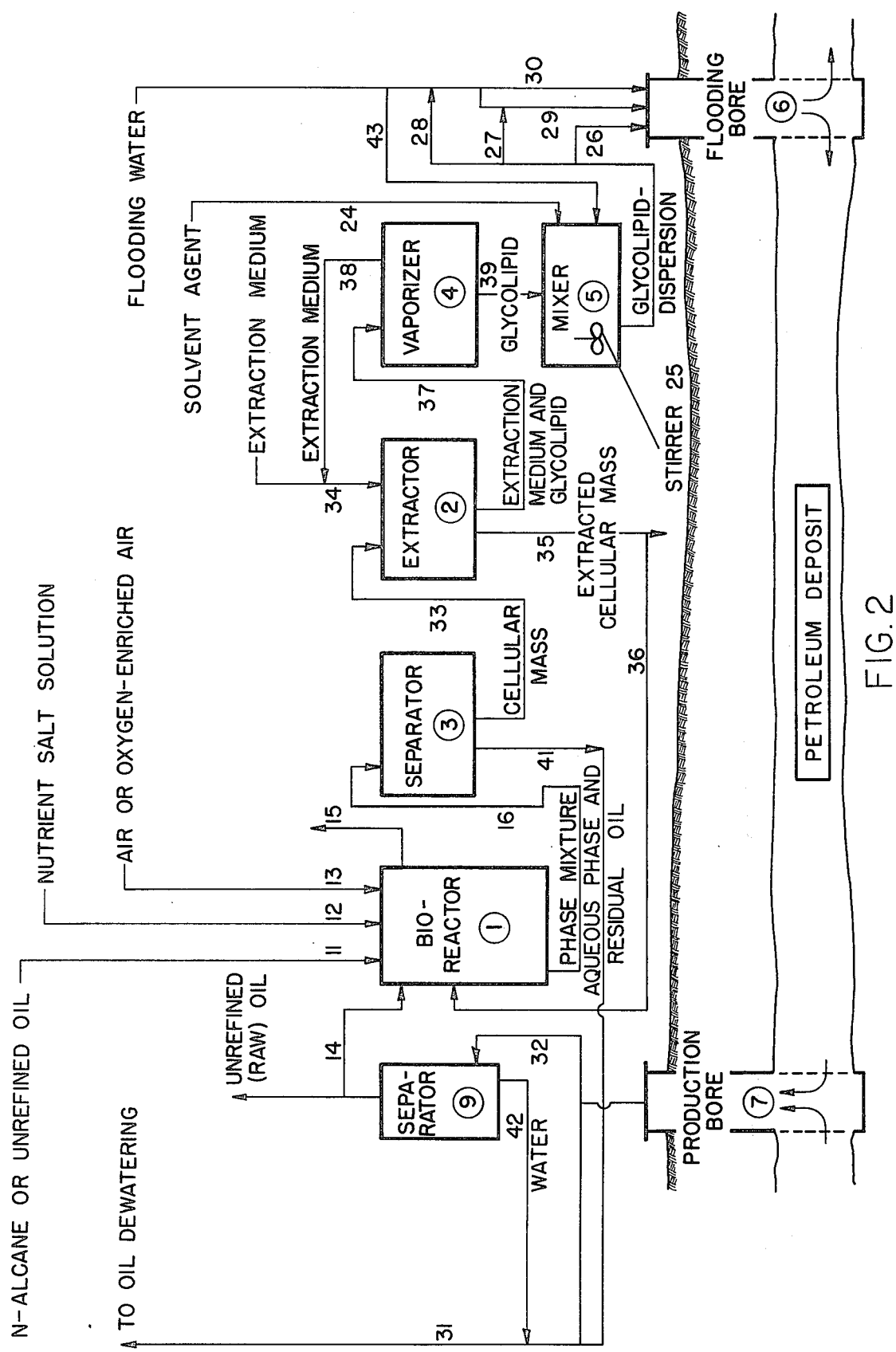

In the embodiment of the invention shown in FIG. 2, reference 1, 11, 12, 13, 14, 15 and 16 have the same meanings as the corresponding reference numerals of FIG. 1. Following separation of the oil/microorganisms in separator unit 3, the cellular mass is introduced through line 33 into extractor unit 2 supplied with extraction medium through line 34. Extracted cellular mass resulting from extractor unit 2 passing through line 35 is recycled to bioreactor 1 through line 36 and combined extraction medium and glycolipid from extractor unit 2 is introduced through line 37 into vaporizer unit 4. Vaporized extraction medium from vaporizer 4 is recycled through line 38 to extractor unit 2 to effect further extraction of glycolipid from the cellular mass introduced therein. Extracted glycolipid passing from vaporizer unit 4 is introduced through line 39 into mixer unit 5 where it is combined with dispersant through line 24 and flooding water through line 43. The resulting glycolipid dispersion is thereafter introduced into flooding bore 6 through any of lines 26, 27, 28 and/or 29. The aqueous phase and residual oil recovered in separator unit 3 is conducted through lines 41 and 31 for further dewatering, as desired. Crude petroleum and flooding water recovered from producing bore 7 are treated in exactly the same manner as described in FIG. 1.

EXAMPLE 1

In the first process stage, a bioreactor equipped with a turbine stirrer is filled with 10 liters of nutrient solution having the composition: $(NH_4)_2HPO_4$ 15 g, $KH_2PO_4$ 5 g, $K_2PO_4.3\ H_2O$ 10 g, $Na_2HPO_4.2\ H_2O$ 5 g, $MgSO_4.7\ H_2O$ 1 g, KCl 1 g dissolved in 10 liters flooding water and 900 g petroleum, 200 g n-alkane mixture having a chain length $C_8$ through $C_{24}$, inoculated with 100 ml inoculum of a Nocardia rhodochrous sp. culture, and cultivated at 30° C., at an aeration rate of 0.5 V/V/m and a rotational speed of 400 rpm. During the growth period, the submersed culture is automatically retained at a pH value of 7.0 with a pH regulating station through the addition of a 12% by volume ammonia solution. After 26 hours a continuous process cycle is initiated and, namely, through the dosing of a nutrient medium having a throughput rate of 0.4 liters per hour. Concurrently, the culture suspension is conducted from this bioreactor into a separator at the same throughput rate for the separation of the unused petroleum and the culture suspension separated from the residual oil is continuously pumped into the second bioreactor.

In the second process stage, this second bioreactor with a constant process volume of 20 liters, is operated at a temperature of 60° C. so as to produce temperature shock, as well as with an aeration rate of 0.2 Vol./Vol./min., a rotational speed of 600 rpm under concurrent automatic pH regulation with a 12% by volume ammonia solution at a pH value of 7.0. From the continuously outflowing culture suspension having a throughput rate of 4 liters per hour, the cellular material is separated through centrifuging, and the aqueous phase which contains the glycolipids having the composition of Example 4 in a concentration of 600 mg/l is directly utilized for the production of a stable aqueous dispersion and then added to the flooding water.

EXAMPLE 2

In the first process stage, a 340 liter bioreactor, equipped with a Kaplan turbine and cylindrical conductor member is filled with 200 liters of nutrient solution having the composition: urea 400 g, $KH_2PO_4$ 200 g, $K_2HPO_4.3H_2O$ 400 g, $Na_2HPO_4.2\ H_2O$ 200 g, KCl 100 g, $MgSO_4.7\ H_2O$ 40 g, dissolved in 200 liters flooding water and 2 kg n-alkane mixture having a chain length $C_{12}$ through $C_{19}$, inoculated with 10 liters inoculum of a Nocardia rhodochrous sp. culture, and cultivated at 30° C., at an aeration rate of 0.5 V/V/m and a rotational speed of 1200 rpm. During the growth period, the submersed culture is automatically maintained at a pH value of 7.0 with a pH regulating station through the addition of a 25% by volume ammonia solution. After 26 hours a continuous process cycle is initiated and, namely, through the dosing of a nutrient medium with a throughput rate of 0.3 liters per hour. Concurrently, the culture suspension is conducted from this bioreactor at the same throughput rate directly into a tubular reactor which is equipped with a two-material jet nozzle and a constant operative volume of 600 liters.

In the second process stage, this bioreactor is maintained at 30° C., an air flow volume of 18 $m^3/h$, and a cycle frequency of 320 per hour at a pH value of 9.5 with an automatic pH regulating station through the addition of a 25% by volume ammonia solution so as to initiate pH shock. From the continuously outflowing culture suspension at a throughput rate of 60 liters per hour there is separated the cellular material through continuous centrifuging, and the aqueous phase which contains the glycolipids having the composition of Example 4 in a concentration of 650 mg/l is directly used for the production of a stable aqueous dispersion and then added to the flooding water.

EXAMPLE 3

In the first process stage, a 340 liter bioreactor, equipped with a Kaplan turbine and a cylindrical conductive member is filled with 200 liters of a nutrient solution having the composition: urea 400 g, $KH_2PO_4$ 200 g, $K_2HPO_4.\ 3\ H_2O$ 400 g, $Na_2HPO_4.2H_2O$ 200 g, KCl 100 g, $MgSO_4.\ 7\ H_2O$ 40 g, yeast extract 20 g dissolved in 200 liters of fresh water and 4 kg n-alkane mixture having a chain length of $C_8$ through $C_{24}$, inoculated with 10 liters inoculum of a mycobacterium phlei culture, and cultivated at 37° C., at an aeration rate of 1.0 Vol./Vol./min. and a rotational speed of 1200 rpm. During the growth period the submersed culture is automatically set to a pH value of 6.8 with a pH regulating station through the addition of a 25% volume ammonia solution. After 20 hours, 160 liters of the submersed culture is pumped into a second bioreactor with 500 liters operative volume and which is equipped with a turbine stirrer. In the second process stage, the culture is further cultivated for 10 hours under the same conditions as in process stage 1. Thereafter, 200 liters of deposit water having a salt content of 10% by weight is added and intensively stirred for an additional 4 hours.

Through the addition of the deposit water with the salt content there is effected the osmotic shock and the glycolipids are released by the cellular material into the culture solution. After the separation of the cellular material, the culture filtrate contains 124.8 g of glycolipids with the following structures:

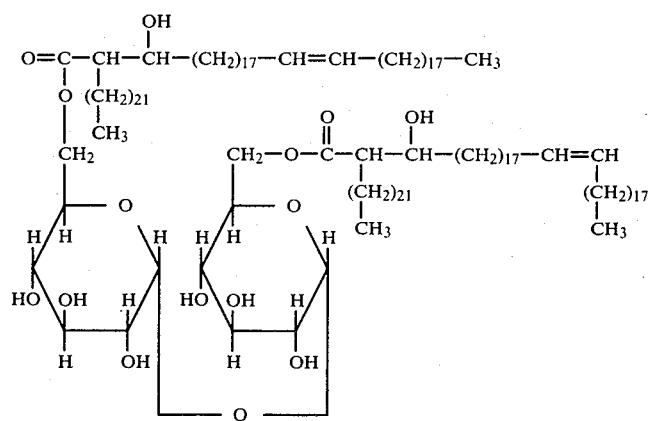

Yield: 74.88 g=60%, relative to the lipid total.

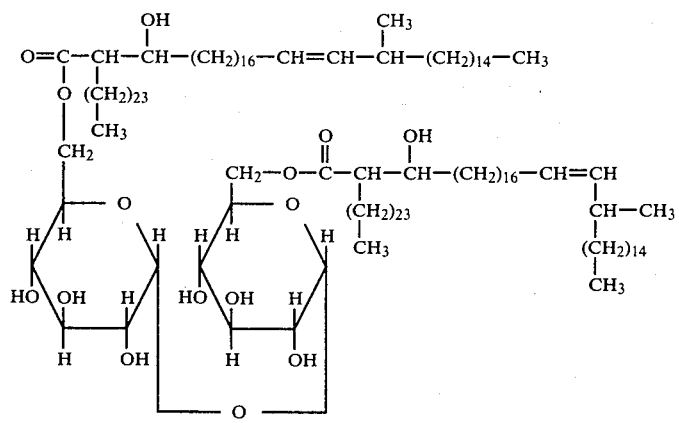

Yield: 49.29 g=40%, relative to the lipid total.

The mixture of these glycolipids from the structures 1 and 2 in the culture filtrate is then directly used for the production of a stable aqueous dispersion and added to the flooding water.

After 160 liters submersed culture has been withdrawn from the bioreactor of the first process stage, the remaining 40 liters of submersed culture is displaced with 160 liters of nutrient salt solution, cultivated for 20 hours under the same conditions as in this process stage, and the semi-continuous recovery of the glycolipids continued in the same manner.

EXAMPLE 4:

In the first process stage, a 14 liter bioreactor, equipped with a Kaplan turbine and cylindrical conductor member is filled with 10 liters nutrient solution having the composition: $(NH_4)_2HPO_4$ 15 g, $KH_2PO_4$ 5 g, $K_2HPO_4 \cdot 3 H_2O$ 10 g, $Na_2HPO_4 \cdot 2 H_2O$ 5 g, $MGSO_4 \cdot 7 H_2O$ 1 g, KCl 1 g dissolved in 10 liters of flooding water and with 100 g n-alkane mixture having a chain length of $C_{12}$ through $C_{19}$, sterilized for 30 minutes at 121° C. and, after cooling to 30° C., inoculated with 100 ml inoculum of a Nocardia rhodochrous sp. culture and cultured at an aeration rate of 0.5 Vol./Vol./min. and a rotational speed of 1200 rpm. During the growth period there is automatically maintained in the submersed culture a pH value of 7.0 with a pH regulation station through the addition of a 12% ammonia solution. The growth is completed after 26 hours.

Thereafter, in a continuous centrifuge at 15000 g the resultant cellular material corresponding to 85 g dried material is separated from the aqueous culture solution. For the isolation of the glycolipids, this obtained cellular material is, in the second process stage, extracted three times with respectively 500 ml n-hexane at 20° C., the combined n-hexane extracts concentrated in a vacuum, and this raw extract adsorbed in a silica gel column having a filled volume of 200 ml. The still present n-alkane mixture of 15 g is elutriated with 250 ml chloroform and, thereafter, the glycolipids with 200 ml acetone. The elutriate is then concentrated in a vacuum and the glycolipids, which are still impure with a yellow coloring agent, are purified through Rechtomatography with the elutriation medium chloroform/acetone in the ratio of 2:1, Vol./Vol. and acetone.

Obtained are 7.2 g of glycolipids having the following structures I:

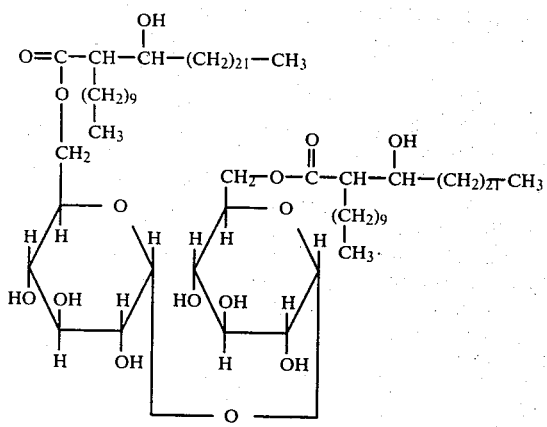

The yield consists of 2.88 g=40%, relative to the total glycolipid.

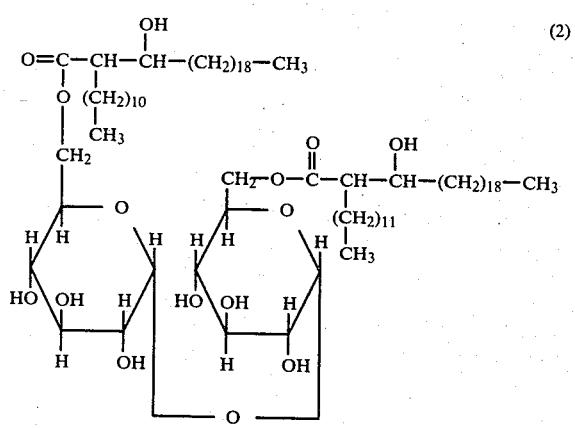

The yield consists of 2.16 g=30%, relative to the total glycolipid.

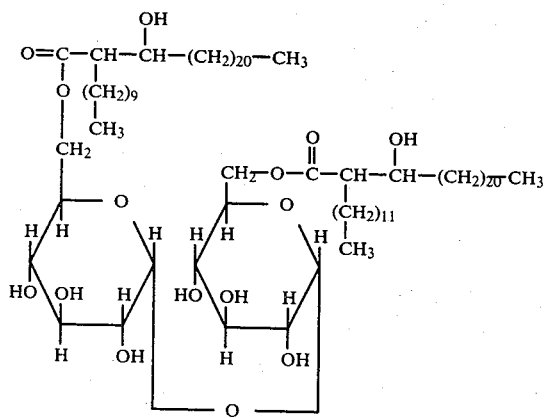

The yield consists of 2.16 g=30%, relative to the total glycolipid.

For the production of the aqueous dispersion, in practice there is utilized the raw extract obtained after the n-hexane extraction, and is then added to the flooding water.

EXAMPLE 5

50 mg glycolipid, which is contained in the raw extract pursuant to the process described in Example 4, is added to 1 liter nutrient salt solution and treated, with concurrent stirring, for 30 minutes with ultrasound (25 KH). This produces a milky appearing dispersion which will not change even after lengthy storing. The dispersion possesses, with respect to petroleum from the petroleum deposit Düste-Valendis, a boundary surface tension of about 5 mN/m which remains constant over more than 100 hours. The thus tested dispersion is utilized as a flooding medium for the improvement of the oil yield in the flooding investigation according to Example 6.

EXAMPLE 6

A flooding core of Bentheimer sandstone, whose diameter is 5.2 cm and whose length is 27 cm has, at 19.4% porosity, a pore volume of 110 ml. Its permeability to water consists of 1600 millidarcy. The core is saturated with 98.9 ml petroleum from the deposit Düste-Valendis (viscosity at 40° C.=26.3 mPa s) and 11.1 ml salt water (viscosity at 40° C.=0.9 mPa s), which contains 28 g/l $CaCl_2$, 9.6 g/l $MgCl_2$ and 102 g/l NaCl; this results in an initial oil saturation of 89.9%.

At a temperature of 40° C., 1143 ml salt water is flooded through the core. Recovered thereby is 40.9 ml oil, which corresponds to 41.4% of the initial oil content. The oil saturation now consists of only 52.7%. Thereafter there is flooded with 749 ml of the dispersion produced in accordance with Example 5, and a further 18.9 ml of oil is obtained. The yield has thus been increased to 60.5%, the oil saturation in the core reduced to 35.5%. Through flooding with 1440 ml salt water after the dispersion there is again recovered 10.5 ml oil and thus the entire yield increased to 71.7%; the residual oil saturation in the core thereafter consists of only 26%. Thus, through the flooding with the dispersion from the oil contained in the core there additionally is recovered 29.4 ml or 51%.

EXAMPLE 7

24 ml glycolipid-containing aqueous phase (40 ml), which is recovered pursuant to Example 1, is added to 960 ml nutrient salt solution and, at concurrent stirring, is treated for 30 minutes with ultrasound (25 kH). There is produced a milky dispersion which will not change even after lengthy storage. This dispersion is utilized for the flooding of a stone core of Bentheimer sandstone which possesses a diameter of 5.2 cm, a length of 27 cm and, at a porosity of 19.1%, a pore volume of 108 ml. The permeability to salt water consists of 1700 Millidarcy. The core is saturated with 98.9 ml petroleum from the deposit Düste-Valendis (viscosity at 40° C.=40 mPa s) and 9.1 ml salt water (viscosity at 40° C.=0.9 mPa s), which contains 28 g/l $CaCl_2$, 9.6 g/l $MgCl_2$ and 102 g/l NaCl; this produces an initial oil saturation of 91.6%. At a temperature of 40° C., flooded through the core is 1264 ml salt water and recovered thereby is 44.5 ml of oil which corresponds to a yield of 45%. The oil saturation now consists of only 50.4%. Thereafter 750 ml dispersion is flooded therethrough and thereby a further 22 ml of oil is recovered. This will increase the oil yield to 67.2%, while the residual oil saturation is reduced to 30%. Through subsequent flooding with 1120 ml salt water there is recovered only an additional 0.2 ml oil; the residual oil saturation is reduced to 29.8%. The additional yield through the glycolipid dispersion consists of 22.2 ml, or 41% of the residual oil still remaining in the core.

The process of the invention affords the technical advantage that, through the utilization of alkane mixtures as C- and energy source, for the first time there are produced glycolipids of predetermined structures through biological synthesis as mixtures through process optimization, enriched, and dosed as aqueous solution to the flood water or directly utilized.

The process pursuant to the invention can initially be carried out with commercial concentrations after the technical effect of the separation of the glycolipids from the cellular material has been determined through the application of the temperature, pH, osmotic shocks in the second process stage. However, also inherent is a technical advantage in that through this biosynthesis under the retention of predetermined parameters, the produced glycolipids can be enriched through extraction with unpolarized, organic solvent media. A further technical advantage consists of in that unrefined oil or petroleum from the petroleum deposits, or from oil shales as n-alkane mixture, can be directly employed after separation of the deposit water at the location of use as hydrocarbon and energy sources for the production of the glycolipid-containing dispersions.

A further advantage of the process of the invention, together with the installation for its effectuation, also consists of in that the separated cellular material can preferably be partially recycled whereby it is possible to effect a saving, particularly in the addition of the nutrient salts. Attendant hereby is also a further technical advantage in that for the process which measures the osmotic shock in the second process stage, there can be used deposit water with an at least 10% salt content directly at the location of the utilization of the glycolipid-containing culture suspension.

The process according to the invention provides for that the glycolipid-containing dispersion can be utilized during the secondary and tertiary recovery of petroleum from petroleum deposits or oil shales through water flooding for increasing the yield of petroleum.

What is claimed is:

1. Process for the flooding of petroleum deposits and oil shale by means of dispersions of non-ionogenic, boundary surface active materials in water as flooding medium, through the utilization of a suitable bioreactor with or without mechanical stirring for a first stage for the production of a growing submerged culture of hydrocarbon enriched microorganisms in a semi- or continuous process under aerobic conditions, under the addition of organic C- sources, inorganic nutrients dissolved in water and occasionally growth materials as well as the addition of air or oxygen-enriched air at a predetermined reaction temperature and constant pH value in the region of between 2 and 9, with a second stage in which the formed effective material is separated from the cell material and, with utilization of the aqueous separating phase with the therein dispersed effective material directly as flooding medium or as addition to the flooding water, characterized in that in the first stage there are produced as the effective material glycolipids with the hydrocarbon enriched microorganism under the utilization of a hydrocarbon mixture of 1 to 35% by volume at a reaction temperature in the range of 20° to 50° C. and at a constant pH value in the range of between 3 and 9, and that thereafter in the second stage the formed glycolipids are separated from the cell material in the form of an aqueous phase through a temperature, pH, or osmotic shock or through extraction and a petroleum deposit and oil shale flooding amount of the aqueous phase with the therein dispersed glycolipids are directly used as a flooding medium or added to the flooding water.

2. Process according to claim 1, wherein the cellular material which is released from the glycolipids is entirely or partially recycled into a growing submersed culture.

3. Process according to claim 1 or 2, wherein there is formed a mixture of non-ionogenic, boundary surface-active glycolipids having the structures pursuant to the following Formula I, in which m=8 through 10 and n=18 through 21 signify:

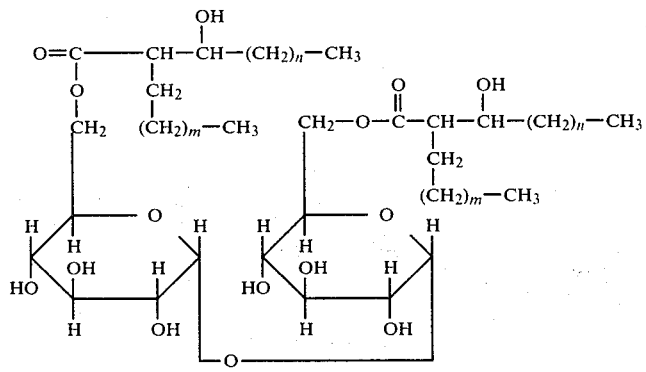

with the utilization of the microorganism Nocardia rhodochrous sp., and as hydrocarbon an alkane mixture with $C_{12}$ through $C_{19}$ or unrefined oil from petroleum deposits or oil shale, and utilized in an aqueous dispersion.

4. Process according to claim 1 or 2, wherein there is formed a mixture of non-ionogenic, boundary surface-active glycolipids having the structures pursuant to the following Formula II, in which m=20 through 22 and n=14 through 17 signify:

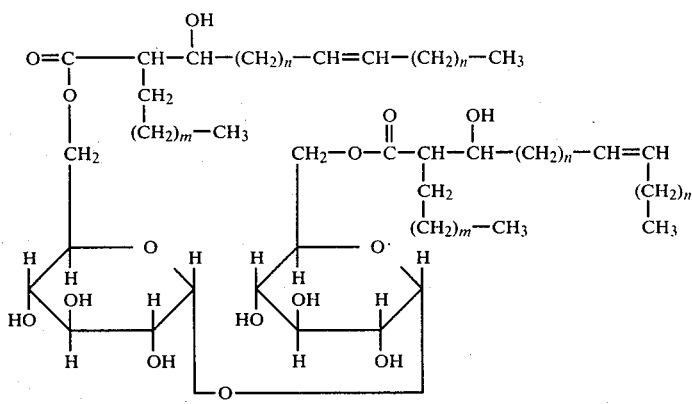

with the utilization of the microorganism Mycobacterium phlei, and as a hydrocarbon material an alkane mixture with $C_8$ through $C_{24}$ or unrefined oil from petroleum deposits or oil shale, and utilized in an aqueous dispersion.

5. Process according to claim 3 or 4, characterized in that the glycolipids having the formula I or II are extracted in the second stage from the cell material of the first stage for the enrichment with an unpolarized organic solvent medium, as well as the extraction medium is separated and preferably reconveyed.

6. Process according to claim 3 or 4, characterized in that the glycolipids having the formula I or II are produced in two stages, whereby the first stage is effectuated at a through-flow rate of 0.1 to 0.7 Vol./Vol./h and a second stage at a through-flow rate of 0.002 through 0.3 Vol./Vol./h.

7. Process according to claim 1, characterized in that utilized as a hydrocarbon mixture is a petroleum-water mixture from the petroleum deposits or oil shales in a concentration of 5 to 35% by volume of petroleum and utilized with water from the deposits or with fresh water.

8. Process according to claim 1, characterized in that there is utilized as the raw oil with an n-alkane content of 5 to 25% by volume having a chain length of $C_8$ through $C_{24}$.

9. Process according to claim 1, characterized in that there is utilized as a hydrocarbon mixture an n-alkane mixture with a chain length of $C_8$ through $C_{24}$ in a concentration of 0.5 to 5% by volume.

10. Process according to claim 1, characterized in that the first stage is carried out at a growth temperature of between 25° to 45° C. and in the second stage a temperature shock at temperatures of between 35° to 70° C.

11. Process according to claim 1, characterized in that in the second stage there is added 50 to 200% by volume of deposit water and/or fresh water having a minimum salt content of 10% by weight so as to reach the osmotic shock.

12. Process according to claim 1, characterized in that the first stage is carried out at a pH value of 4 through 8 and in the second stage a pH shock at a pH value of between 8 to 10.

13. Process according to claim 1, characterized in that the growth and the product formation of the cell material of the microorganism is controlled through the addition of alkalis or acids for adjustment of the constant pH value.

14. Process according to claim 1, characterized in that the aqueous nutrient solution of the first stage contains ammonium and/or nitrate salts and/or urea as a nitrogen source as well as others for the growth and for the product formation of the cell material of the microorganism necessary inorganic salts and growth materials such as yeast extract or meat extract.

15. Process according to claim 1, characterized in that the air or oxygen-enriched air with an oxygen content of between 20 to 60% by volume with an aeration rate of 0.1 to 2.0 Vol./Vol./min. and prefereably with 0.5 to 1.5. Vol./Vol./min. in the process is added in the first or second stage.

16. Process according to claim 1, characterized in that the aqueous dispersion of the glycolipids have added thereto solvent means for stablization.

17. Process according to claim 1, characterized in that the aqueous dispersion of the glycolipids are stabilized prior to dosing to the flood water through intensive stirring and/or through ultrasound treatment.

* * * * *